United States Patent [19]

Müller et al.

[11] Patent Number: 5,374,704
[45] Date of Patent: Dec. 20, 1994

[54] PURE, IN PARTICULAR CATALYST-FREE POLYURETHANES

[75] Inventors: Hanns-Peter Müller, Odenthal; Rolf Dhein, Krefeld; Herbert Hugl, Bergisch Gladbach; Heinz Pudleiner, Krefeld, all of Germany

[73] Assignee: Bayer Aktiengesellschaft, Leverkusen, Germany

[21] Appl. No.: 166,760

[22] Filed: Dec. 14, 1993

[30] Foreign Application Priority Data

Dec. 23, 1992 [DE] Germany .............................. 42343782
May 7, 1993 [DE] Germany .............................. 4315173

[51] Int. Cl.$^5$ .............................................. C08G 18/10
[52] U.S. Cl. .............................................. 528/66
[58] Field of Search .............................................. 528/66

[56] References Cited

U.S. PATENT DOCUMENTS

| | | | |
|---|---|---|---|
| 4,332,927 | 6/1982 | Simone | 528/58 |
| 5,133,742 | 7/1992 | Pinchuk | 623/1 |

FOREIGN PATENT DOCUMENTS

| | | |
|---|---|---|
| 3643465 | 7/1988 | Germany . |
| 9204390 | 3/1992 | WIPO . |

*Primary Examiner*—Maurice J. Welsh
*Attorney, Agent, or Firm*—Joseph C. Gil; N. Denise Brown

[57] ABSTRACT

The present invention is directed to pure polyurethanes which are biocompatible. These pure polyurethanes comprise the reaction product of:

a) a pre-adduct containing NCO groups and comprising the reaction product of
   i) a diisocyanate selected from the group consisting of aliphatic diisocyanates, cycloaliphatic diisocyanates, and mixtures thereof, with
   ii) a macrodiol having a molecular weight of from 500 to 10,000 wherein said components i) and ii) reacted at temperatures of from 90°–150° C.; with b) a chain extender having a molecular weight of from 62 to 400 and being selected from the group consisting of aliphatic diols, cycloaliphatic diols, and mixtures thereof, and optionally, c) additional diisocyanate selected from the group consisting of aliphatic diisocyanates, cycloaliphatic diisocyanates, and mixtures thereof, wherein said component c), when added, is added either simultaneously with component b) or separately from component b), the quantities of components a)i), a)ii), and c) being such that the molar ratio of diisocyanate to macrodiol is from 1.5:1 to 22:1, and the reaction of components a) and b) and optionally component c) is conducted at temperatures of from 90° to 230° C., with the proviso that the reaction conditions are maintained until said polyurethane has a melt viscosity of at least 2500 mPa.s at 120° C.

7 Claims, No Drawings

PURE, IN PARTICULAR CATALYST-FREE POLYURETHANES

BACKGROUND OF THE INVENTION

The present invention relates to pure polyether urethanes and polyester urethanes based on aliphatic and/or cycloaliphatic diisocyanates. This invention also relates to the use of such pure polyurethane synthetic materials for biomedical applications. Thermoplastic polyurethane elastomers (TPU) have long been known (Kunststoff Handbuch Vol 7 (1983) ISBN 3-446-13614-2, p.428 ff).

The use of such TPU for biomedical applications is described, e.g., by Gogolewski in Colloid Polym. Sci 267 757–785 (1989). In particular, the chemistry, structure-property relations, tissue-material interaction, surface properties, biomedical use, and compatibility properties of biomedical polyurethanes are discussed. On page 782, Gogolewski concludes that: "Biocompatible and blood compatible polyurethane elastomers with unique physical and mechanical properties resulting from the hard-segment-soft-segment microphase segregation, are materials of choice for a number of biomedical applications".

Gogolewski further indicates that for biomedical applications, the two-step solution polymerization process which leads to polyurethanes having better physical characteristics, is preferred to one-step solution or melt polymerizations. The purity of reactants and polymerization media is critical to the final properties of polyurethanes. Factors affecting the purity of biomedical polyurethanes include the effective removal from the polymer of catalyst residues, low molecular weight fractions, processing aids, etc. The purity of the biomedical polyurethane determines to a great extent their in vivo performance (i.e. biocompatibility, blood compatibility, molecular stability).

Research on polyurethanes has continued since then, with the goal of developing the 'ultimate' biomedical polyurethanes of tomorrow.

In recent years, many authors and companies have applied for patents for so-called biocompatible polyurethanes. For instance, G. Wick, Akzo GmbH, in German Auslegeschrift 3,643,465 (1986) describes a process for the production of biocompatible polyurethanes by the reaction of cycloaliphatic diisocyanates with a macrodiol to form a pre-adduct exhibiting NCO groups, wherein the diisocyanate to macrodiol molar ratio is from 3:1 to 33:1. Chain extension of the pre-adduct is effected with a mixture consisting of low-molecular-weight aliphatic diol and an aliphatic and/or cycloaliphatic macrodiol, wherein the aliphatic diol contains trimethylhexanediol within the mixture of the chain extenders. The addition of tin catalysts is prescribed in the embodiments given as examples.

In European Patent 0,461,375 and U.S. Pat. No. 5,133,742, a thermoplastic polyurethane (TPU) is described which is suitable for medical purposes. The preferred TPU described is synthesized from polycarbonate diol (molecular weight 1898), MDI, and 1,4-butanediol.

In PCT WO 92/04390, M. SZYCHER, Polymedica Industries Inc., describes other biostable polyurethanes. The polyurethanes described therein are synthesized from organic diisocyanates which are preferably the reaction product of aliphatic and/or cycloaliphatic diisocyanates with polycarbonate diol, and chain-extended with diol, diamine or a mixture of diamine and alkanolamine. Example 1 substantiates the use of tin catalysts.

E. Müller discovered as long ago as 1969 (see Angew. Makromol. Chemie 14 (1970), 75–86) that polyurethane elastomers having the highest resistance to hydrolysis are obtained from 1,6-hexanediol polycarbonate.

Gogolewski indicates that aliphatic polyurethanes are to be preferred to the aromatic polyurethanes for biomedical purposes.

However, aliphatic or cycloaliphatic polyisocyanates react with diol components too slowly. This resulted in the addition of catalysts to the reaction mixtures according to all known processes of the state of the art. Tin octoate, dibutyl tin dilaurate and/or tertiary amines, such as, for example, diazabicyclooctane (DABCO), have proved to be useful as catalysts.

Therefore, it is an object of the present invention to make available polyurethanes which are as free as possible from additives and which are produced without the addition of catalysts. The polyurethanes should be synthesized from aliphatic and/or cycloaliphatic diisocyanates, and as a result constitute pure polyurethanes which can also be used in medical technology.

All known processes of the state of the art which are employed to produce TPUs operate at temperatures which are as low as possible in order to avoid any unwanted side reactions. The most important side reactions to be avoided are the dimerization of diisocyanates, trimerization, formation of carbodiimide, formation of allophanate and formation of biuret.

In the synthesis of TPUs, one particular factor which must be taken into account is the formation of allophanate with the occurrence of molecular branching. Kunststoffhandbuch Vol. 7 Polyurethane (1983) at page 82, suggests that these reactions can also be carried out without catalysts at temperatures of around 120° to 140° C.

Synthesis of TPUs is customarily effected via NCO prepolymers. According to D. Dieterich in Houben-Weyl, Vol E 20, pp 1613–1617, it is the catalysts which influence the composition of the products. The temperature (i.e. below 100° C.), the reaction time and the mode of addition play a less significant role in the composition.

From the publications disclosed hereinabove, it is evident that for the synthesis of TPUs via NCO prepolymers and semiprepolymers temperatures below 100° C. are preferred.

For the production of transparent, non-yellowing elastomers, and in particular for biomedical applications, prepolymers based on 1,6-bis-[isocyanate]-hexane (i.e. HDI) or 5-isocyanate-3-(isocyanatemethyl)-1,3,3-trimethylcyclohexane (i.e. IPDI) can be used. For glycol extension of these prepolymers, a considerable amount of catalysis has to be effected (see, for example, D. Dieterich in Houben-Weyl, Vol E 20, p. 1637 and the bibliography therein). From the processes known from the literature, one of ordinary skill in the art would conclude that aliphatic TPUs cannot be produced without the use of catalysts.

For these reasons, it is surprising that in accordance with the present invention it is possible to produce particularly pure aliphatic TPUs of high mechanical quality by operating at temperatures above 100° C. without the addition of catalysts.

DESCRIPTION OF THE INVENTION

The present invention is directed to pure polyurethanes which are biocompatible. These pure polyurethanes comprise the reaction product of:

a) a pre-adduct containing NCO groups and comprising the reaction product of
   i) a diisocyanate selected from the group consisting of aliphatic diisocyanates, cycloaliphatic diisocyanates, and mixtures thereof, with
   ii) a macrodiol having a molecular weight of from 500 to 10,000 wherein said components i) and ii) reacted at temperatures of from 90°–150° C.; with
b) a chain extender having a molecular weight of from 62 to 400 and being selected from the group consisting of aliphatic diols, cycloaliphatic diols, and mixtures thereof, and optionally,
c) additional diisocyanate selected from the group consisting of aliphatic diisocyanates, cycloaliphatic diisocyanates, and mixtures thereof, wherein said component c), when added, is added either simultaneously with component b) or separately from component b), the quantities of components a)i), a)ii), and c) being such that the molar ratio of diisocyanate to macrodiol is from 1.5:1 to 22:1, and the reaction of components a) and b) and optionally component c) is conducted at temperatures of from 90° to 230° C., with the proviso that the reaction conditions are maintained until said polyurethane has a melt viscosity of at least 2500 mPa.s at 120° C., and optionally, said polyurethane undergoes completion of the polyaddition reaction at elevated temperatures of up to 240° C.

This invention also relates to the use of the pure, compatible polyurethane synthetic materials for the production of implants, and in particular for the manufacture of catheters and tubes, for the manufacture of blood bags, foils for medical application, adhesives and any molded bodies as orthopaedic materials. Of course, such polyurethanes may also find applications in other fields outside the area of medical technology.

In addition, this invention relates to a process for the production of the pure, biocompatible polyurethanes, optionally dissolved in an organic solvent. This process comprises the steps of:

a) forming a pre-adduct containing NCO groups by reacting
   i) a diisocyanate selected from the group consisting of aliphatic diisocyanate, cycloaliphatic diisocyanates, and mixtures thereof, with
   ii) a macrodiol having a molecular weight of from 500 to 10,000, at temperatures of from 90° to 150° C.,
b) adding a chain extender to the pre-adduct, wherein said chain extender is selected from the group consisting of aliphatic diols and cycloaliphatic diols, and, optionally,
c) adding additional diisocyanate either simultaneously with the chain extender or separately from the chain extender, wherein the diisocyanate is selected from the group consisting of aliphatic diisocyanates, cycloaliphatic diisocyanates, and mixtures thereof, wherein the quantities of diisocyanate to macrodiol are such that the molar ratio of the diisocyanate to the macrodiol is from 1.5:1 to 22:1, and the addition of the chain extender, and, optionally, the additional diisocyanate to the pre-adduct is conducted at temperatures of from 90° to 230° C., with the proviso that the reaction conditions are maintained until the produced polyurethane has a melt viscosity of at least 2500 mPa.s.

This process can additionally comprise the step of d) heating the produced polyurethane to temperatures up to 240° C. to complete the polyaddition reaction.

Additional details regarding the process and procedures are set forth hereinbelow.

The macrodiols used in the synthesis of the pre-adduct (i.e. NCO semiprepolymer) include those which preferably have molecular weights of from 600 to 2000. In this respect, it is possible to use the known polyethers based on, for example, tetrahydrofuran or ethylene oxide/propylene oxide; polyesters based on, for example, adipic acid and diols or polycarbonates, such as, for example, 1,6-hexanediol polycarbonate; polyesters based on for example, $\epsilon$-caprolactone, cycloaliphatic polycarbonates or mixtures thereof, such as those described in principle in the summary given by Gogolewski in Colloid Polym. Sci, 267, 757–785 (1989), herein incorporated by reference. In particular, see, for example page 762 which described PEO, PTMO, PPO, PIB, PEA, PCL, PDMS-OH, PBD. It is also possible to use polyisobutylenes and/or polysiloxanes concomitantly with the macrodiols identified hereinabove.

The preferred diisocyanates include, for example, the known aliphatic and cycloaliphatic diisocyanates such as, for example, 4,4'-dicyclohexylmethane diisocyanate (i.e. r-MDI of reduced MDI), trans-1,4-cyclohexane diisocyanate (CDI), isophorone diisocyanate (IPDI), hexamethylene diisocyanate (HDI), 1,1,6,6-tetrahydroperfluorohexamethylene diisocyanate, tetramethylxylylene diisocyanate (TMXDI) or dimeryl diisocyanate (DDI). If r-MDI is used, then both the technical mixtures (20% tt/50% tC/30% C,C) and the enriched mixtures with higher t/t (trans/trans) content may be used. Pure trans/trans may also be used.

Suitable chain extenders include, for example, the known difunctional or polyfunctional compounds which have active hydrogen atoms, wherein said compounds have a molecular weight of from 62 to 400. If trifunctional or tetrafunctional compounds are used, then crosslinked polyurethanes result as casting systems. If difunctional compounds are used, such as, for example, ethylene glycol, diethylene glycol, dipropylene glycol, 1,4-butanediol, 1,6-hexanediol, trimethyl hexanediol, 1,8-octanediol, neopentyl glycol or 1,12-dodecanediol, cyclohexyldimethanol, 1,4-cyclohexanediol or perhydrobisphenol-A, then thermoplastic polyurethane synthetic materials result. Trifunctional crosslinking agents include, e.g., glycerine, and trimethylolpropane. Crosslinking agents of higher functionality include, e.g., pentaerythritol or sorbitol.

Both the reaction to form the pre-adduct (i.e. semiprepolymer) and the chain extension can be carried out in accordance with procedures which are well known in polyurethane chemistry. The macrodiol is placed in a boiler, and alehydrated at 120° C. under a vacuum. Diisocyanate is then added, in quantities such that the molar ratio of diisocyanate to macrodiol is from 1.5:1 to 22:1, thereby forming the prepolymer or the semiprepolymer. In general, the reaction is carried out in the absence of a solvent. However, it is possible to carry out the reaction in the presence of a solvent.

For chain extension, in general, a small excess of NCO groups relative to OH groups of the chain extender is used. It is preferred that the ratio of NCO groups to OH groups in a mixture is from 1.15:1 to 1.01:1. However, it is also possible to use either equivalent amounts or an excess of OH groups. Monofunctional chain-reaction terminators are also possible to use. Since it is known that the chain extenders form the hard segments with the diisocyanates, the proportion of diisocyanate in the parent materials is important. In this manner, it is possible to control mechanical properties of the produced TPUs such as hardness, softening range, plastic range and melting range by means of the proportion by weight of the diisocyanate in the final product.

An essential aspect of the claimed invention is working without catalysts. The semiprepolymer is then mixed. With the chain extenders, and heated to 130°–180° C., and preferably 130°–150° C. In this particular process, the polymer synthesis is controlled via the NCO number and the viscosity. When a viscosity of 2500 mPa.s, determined at 120° C., has been attained, the deposit is poured out and polyaddition is carried through to a conclusion in the heating chamber.

In operation, however the process is implemented in such a way that semiprepolymers and chain extenders are mixed using suitable mixing units (i.e. nozzles, mixer head, static mixer). The homogeneous mixture obtained therefrom is conveyed across a heatable tubular reactor via suitable pumps. If necessary, chain-reaction terminators are charged, and after the desired viscosity has been attained, the mixture is conveyed to a screw machine (e.g., ZSK 32). The polyaddition reaction is optionally carried through to completion in a temperature range of 140°–250° C., and preferably 140°–240° C. Homogeneous, speck-free polymer strands are extruded from the extruder and granulated after cooling. The formed granulated material can be post-tempered in silos prior to further use.

Technically speaking, reactive extrusion can be employed equally as well as the so-called band or band-extrusion process. With these processes the reaction mass is deposited on a band. The material deposited on this band then passes through various temperature zones, thereby completing the reaction.

In a further mode of proceeding according to the invention, the macrodiol is placed in a suitable boiler, and dehydrated subject to stirring and vacuum at 120° C., After this, the entire quantity of aliphatic and/or cycloaliphatic diisocyanate is added under nitrogen, and the boiler is heated to 150° C. After about 1 hour, the NCO (semi)prepolymer has formed. It is possible to check on the formation of the NCO prepolymer by titration of the NCO content. After this, the boiler is charged, while continuously being heated, with the calculated quantity of diol chain-extender, and the resulting melt of the TPU is stirred for a further hour at 210°–240° C. The highly viscous, easily stirrable melt is then discharged onto teflon plates. In this way, a polyurethane is obtained which at room temperature is non-sticky, clear and colorless.

The mode of operation disclosed hereinabove can always be applied when operating with isocyanate indices >100.

However, if it is desired to synthesize TPUs with isocyanate indices <100, then synthesis via the following steps should be carried out in the case of the boiler method described hereinabove. Placement of the macrodiol into the boiler, followed by dehydration as described hereinabove. Then 1,5–3 mol. diisocyanate are charged to the calculated quantity of macrodiol, and allowed to react off to form the NCO prepolymer (at temperatures of up to 150° C.). Following the check on the NCO content, the entire calculated quantity of the chain extender is added to the deposit. In the process, the contents of the boiler are heated up to 160° C. by the exothermic reaction. After the exothermic reaction has died down, the calculated quantity of diisocyanate is charged at 150°–240° C., in the presence of heat. The melt of the TPU is stirred for a further I hour, and then the melt is caused to flow to a cooling bath (e.g., a water bath or a cooled Kaiser band). In this way TPUs with isocyanate indices <100 are synthesized.

The phrase isocyanate index as used herein is defined as:

$$\text{isocyanate index} = \frac{\text{moles isocyanate}}{\text{moles hydroxyl}} \times 100$$

A further variation of this process according to the invention, consists of preparing the prepolymer from the macrodiol and the diisocyanate wherein the molar ratio of diisocyanate to macrodiol is 1.5:1. In this process, NCO prepolymers are formed which possess pre-extended soft segments over diisocyanates. This mode of proceeding can be implemented according to either of the processes described hereinabove to achieve isocyanate indices of >100, or isocyanate indices of <100.

It is an advantage that pure, biocompatible polyurethanes are obtained according to the process of the present invention. The concomitant use of lubricants in the production of the polyurethanes is also possible. A preferred lubricant to be used is the stearyl amide of ethylene diamine (i.e. ®Hoechstwachs C, EBS-Wachs Rhenax 12).

Obviously, polyurethanes which are to be used as molded bodies for implantation purposes should be prepared from parent materials of high purity. This is particularly true of the diisocyanates and low-molecular-weight chain extenders employed.

The polyurethanes produced according to the invention can be processed into molded bodies in accordance with various customary processes such as, for example, extrusion, injection molding, tube extrusion, and foil extrusion. These molded bodies, and especially tubes, are non-buckling, non-sticky, transparent, speck-free, soft or stiff, flexible and, in particular, sterilizable (superheated steam, EO, γ-radiation).

It is also possible to put the polyurethane into solution and then to work from the solution (i.e. dipping, casting, coagulation processes). Suitable solvents include, for example, chloroform, dimethylformamide, dimethylacetamide, N-methylpyrrolidone or toluene/isopropanol mixtures.

It is particularly advantageous that, it is possible to vary the surface composition in chemical respects of the molded bodies produced from these polyurethanes without impairing its outstanding mechanical properties or its biocompatibility. This is accomplished by slightly varying the setting of the molar ratio of NCO groups to OH groups. For example, by regulation of the isocyanate excess it is possible to change the reactivity of the polyurethane with the other groups that react with isocyanate. As a result, it is possible to influence the compatibility of and the degree to which the polyurethane bodies combine with the environment. For instance, by altering the number of the isocyanate groups which remain capable of reacting, it is possible to effect various interactions between the polyurethane molded body and the environment into which the biocompatible molded body is implanted.

The pure, catalyst-free biocompatible polyurethanes are suitable for applications both in veterinary and in human medicine, as well as in other areas of technology. Other areas include, for example, fadeproof foils for the interior fittings of motor vehicles, laminated glass, molded bodies, injection-molded articles, sealing materials, composite materials or packaging material.

The invention is further illustrated by reference to the examples given hereinbelow.

The following examples further illustrate details for this invention. The invention, which is set forth in the foregoing disclosure, is not to be limited either in spirit or scope by these examples. Those skilled in the art will readily understand and know that variations of the conditions of the following procedures can be used. Unless otherwise noted, all temperatures are degrees Celsius and all parts are parts by weight.

EXAMPLES

By Way of parent materials use is made of:
®Desmophen 2020 (Bayer AG): 1,6-hexanediol polycarbonate, molecular weight 2000, OH number 56
®Desmodur W (Bayer AG) (i.e. reduced MDI): 4,4'-dicyclohexylmethane diisocyanate (~20% t,t/~50% t,c/~30% c,c) ®Terathane 1000 (DuPont): Polytetrahydrofuran, molecular weight 1000, OH number 112
Polyether L 1515: a polyether based on propylene glycol with 87% PO and 13% EO, molecular weight 750, OH number 150
Polyether L 5050: a polyether based on propylene glycol with 50% PO and 50% EO by way of mixing block, molecular weight 2000, OH number 56
Polywachs 56: a polyether based on diethylene glycol with 100% EO, molecular weight 2000, OH number 56 The proportion of hard segment was calculated from the sum of diisocyanate and short-chain diol (see also Houben-Weyl, Vol E 20, p 1568 ff).

Example 1

Preparation of the pre-adduct containing isocyanate groups: 800 g (0.4 mol) of Desmophen 2020 was alehydrated to form a melt at 20° C. and 30 mbar in a 2-1 ground glass beaker while stirring. The temperature was then lowered to 80° C., and 927 g (3.54 mol) Desmodur W were added. Stirring was continued for 5 h at 110° C. and 20 mbar. The NCO content was determined from a sample taken from the deposit. The NCO content was 7.9% NCO (vs. a calculated value of 7.95%).

Chain extension of pre-adduct: The temperature of the preadduct formed hereinabove was lowered to 90° C., and 20 g Höchstwachs C and 274 g (3.04 mol) 1,4-butanediol were added. Then the temperature was allowed to rise slowly, for about 45 minutes, to 130° C. and the deposit was poured out onto a teflon plate. The NCO content was determined once again after pouring out. The NCO content was 1.8% NCO. The polyaddition reaction was then completed by tempering for 15 h at 130° C.

The produced sheet material was cut into pieces, ground into granulated material, and homogenized for manufacture as granulated material in an extruder at 190° C. and 20 bar. This material contained 40% soft segment and 60% hard segment. The processing temperature for injection molding amounted to 200° C.

Examples 2–18

These examples followed the same procedure as set forth hereinabove in Example 1, except for the following details.

Example 2

A TPU having 50% soft segment and 50% hard segment was obtained from 1000 g (0.5 mol) Desmophen 2020, and 790 g (3.02 mol) Desmodur W, as well as 218 g (2.42 mol) 1,4-butanediol.

Example 3

A TPU having 55% soft segment and 45% hard segment was obtained from 1100 g (0.55 mol) Desmophen 2020, and 721 g (2.75 mol) Desmodur W, as well as 189 g (2.1 mol) 1,4-butanediol.

Example 4

A TPU having 60% soft segment and 40% hard segment was obtained from 1200 g (0.6 mol) Desmophen 2020 and 645 g (2.46 mol) Desmodur W as well as 161 g (1.79 mol) 1,4-butanediol.

Example 5

A TPU having 65% soft segment and 35% hard segment was obtained from 1300 g (0.65 mol) Desmophen 2020 and 570 g (2.17 mol) Desmodur W as well as 132 g (1.47 mol) 1,4-butanediol.

Example 6

A TPU having 40% soft segment and 60% hard segment was obtained from 800 g (0.4 mol) Desmophen 2020 and 867 g (3.31 mol) Desmodur W as well as 333 g (2.82 mol) 1,6-hexanediol.

Example 7

A TPU having 50% soft segment and 50% hard segment was obtained from 1000 g (0.5 mol) Desmophen 2020 and 736 g (2.81 mol) Desmodur W as well as 264 g (2.24 mol) 1,6-hexanediol.

Example 8

A TPU having 55% soft segment and 45% hard segment was obtained from 1100 g (0.55 mol) Desmophen 2020 and 675 g (2.57 mol) Desmodur W as well as 230 g (1.95 mol) 1,6-hexanediol.

Example 9

A TPU having 60% soft segment and 40% hard segment was obtained from 1200 g (0.6 mol) Desmophen 2020 and 605 g (2.31 mol) Desmodur W as well as 196 g (1.66 mol) 1,6-hexanediol.

Example 10

A TPU having 40% soft segment and 60% hard segment was obtained from 800 g (0.4 mol) Desmophen 2020 and 822 g (3.7 mol) isophorone diisocyanate as well as 378 g (3.2 mol) 1,6-hexanediol.

Example 11

A TPU having 50% soft segment and 50% hard segment was obtained from 1000 g (0.5 mol) Desmophen 2020 and 698 g (3.15 mol) isophorone diisocyanate as well as 302 g (2.56 mol) 1,6-hexanediol.

Example 12

A TPU having 60% soft segment and 40% hard segment was obtained from 1200 g (0.6 mol) Desmophen 2020 and 578 g (2.6 mol) isophorone diisocyanate as well as 227 g (1.92 mol) 1,6-hexanediol.

Example 13

A TPU having 45% soft segment and 55% hard segment was obtained from 900 g (0.9 mol) Terathane 1000 and 884 g (3.38 mol) Desmodur W as well as 216 g (2.4 mol) 1,4-butanediol.

Example 14

A TPU having 50% soft segment and 50% hard segment was obtained from 1000 g (1 mol) Terathane 1000 and 816 g (3.11 mol) Desmodur W as well as 185 g (2.05 mol) 1,4-butanediol.

Example 15

A TPU having 40% soft segment and 60% hard segment was obtained from 800 g (0.8 mol) Terathane 1000 and 945 g (3.61 mol) Desmodur W as well as 243 g (2.7 mol) 1,4-butanediol.

Example 16

A TPU having 40% soft segment and 60% hard segment was obtained from 800 g (1.07 mol) Polyether L 1515 and 974 g (3.72 mol) Desmodur W as well as 226 g (2.52 mol) 1,4-butanediol.

Example 17

A TPU having 40% soft segment and 60% hard segment was obtained from 800 g (0.4 mol) Polyether L 5050 and 925 g (3.54 mol) Desmodur W as well as 274 g (3.04 mol) 1,4-butanediol.

Example 18

A TPU having 40% soft segment and 60% hard segment was obtained from 800 g (0.4 mol) Polywachs 56 and 925 g (3.54 mol) Desmodur W as well as 274 g (3.04 mol) 1,4-butanediol.

Example 19

(Comparative example, re-adjustment of Example 5 from PCT WO 92/04390): 1000 g (0.5 mol) hexanediol polycarbonate (Desmophen 2020 Bayer AG) were dehydrated at 110° C. and 20 mbar while stirring for 1 h. Then at 80° C., 275 g (1.05 mol) Desmodur W (reduced-MDI) and 0.1 ml DBTL (dibutyl tin dilaurate) were added and stirred for a further 3 h at 110° C. and 20 mbar. Subsequent to this, the temperature was lowered to 80° C. and 59 g (0.5 mol) of 1,6-hexanediol chain extender were added. As a consequence of the hardening of the material that set in at once, the deposit was immediately distributed onto a teflon plate using a spatula and tempered in a heating chamber at 110° C. for 5 h. A soft polymer was formed which under the microscope did not melt up to a temperature of 300° C. and which exhibited decomposition reactions starting a temperatures above 300° C. The polymer was not soluble in methylene chloride, DMF, DMAC or N-methylpyrrolidone.

Example 20

(Re-adjustment of Example 19 under the conditions of the present invention): The process described hereinabove in Example 19 was followed, except that no tin catalyst was used and the chain-extension reaction was carried out under the conditions of Example 1. After tempering at 130° C., a material is obtained which when heated is still stringy but at room temperature is solid, non-sticky and very soft. This polyurethane is soluble in methylene chloride, DMF, MAC or NMP. The produced material contained 75% soft segment and 25% hard segment.

Example 21

900 g (0.45 mol) Desmophen 2020 were melted in a 2-l ground glass beaker and dehydrated while stirring for 30 minutes at 120° C. and 15 mbar. 176.9 g (0.675 mol) Desmodur W were then added. This mixture was heated under $N_2$ to 150° C. Stirring continued for 1 h at this temperature, and the NCO content was measured. The NCO content amounted to 1.78% (vs. a calculated value of 1.76%). To that prepolymer, an additional 264.1 g (1.01 mol) Desmodur W and 140 g (1.19 mol) 1,6-hexanediol were added. Subsequently, the entire deposit was heated to 230° C. and stirred for a further 30 minutes at this temperature. The highly viscous, stirrable melt was poured onto a teflon plate. A clear, non-sticky polyurethane was obtained.

Isocyanate index: 103
40 wt % hard segment
60 wt % soft segment

Example 22

800 g (0.8 mol) Terathane 1000 were melted in a 2-l ground glass beaker and dehydrated while stirring for 30 minutes at 120° C. and 20 mbar. Then, 945 g (3.6 mol) Desmodur W were added while heating under $N_2$ to a temperature of 150° C. After stirring continued for 1 h at this temperature, the NCO content was determined and found to be 13.8% (vs. a calculated value 13.5%). Then, 243 g (2.7 mol) 1,4-butanediol were dropped in at 150°-200° C. and stirring was continued for 1 hour at 200°-210° C. The highly viscous, easily stirrable melt was poured onto a teflon plate. At room temperature a non-sticky, clear, colorless polyurethane having an NCO content of 0.46% (vs. a calculated value of 0.42%) was obtained.

Isocyanate index: 103
60 wt % hard segment
40 wt % soft segment

Example 23

800 g (0.8 mol) Terathane 1000 were melted in a 2-l ground glass beaker and dehydrated while stirring for 30 minutes at 120° C. and 20 mbar. After, 524 g (2 mol) Desmodur W were added while heating to 150° C. The NCO content was determined to be 7.7% (vs. a calculated value 7.6%). Rapidly 251 g (2.79 mol) of butanediol were added to the deposit. After this, the contents of the flask heated itselves from 130° C. up to 154° C., Subsequently, 406 g (1.55 mol) Desmodur W were added at 150°-200° C., followed by further stirring for 1 hour at 200°-210° C. The melt was then poured onto a teflon plate. At room temperature the product was clear, colorless and non-sticky.

Isocyanate index: 99
60 wt % hard segment
40 wt % soft segment

Although the invention has been described in detail in the foregoing for the purpose of illustration, it is to be understood that such detail is solely for that purpose and that variations can be made therein by those skilled in the art without departing from the spirit and scope of the invention except as is may be limited by the claims.

What is claimed is:

1. Pure polyurethanes comprising the reaction product of
   a) a pre-adduct containing NCO groups and comprising the reaction product of
      i) a diisocyanate selected from the group consisting of aliphatic diisocyanates, cycloaliphatic diisocyanates, and mixtures thereof, with
      ii) a macrodiol having a molecular weight of from 500 to 10,000 in a molar ratio of component i) to component ii) of from 1.5:1 to 22:1, said components i) and ii) reacted at temperatures of from 90°–150° C.; with
   b) a chain extender having a molecular weight of from 62 to 400 and being selected from the group consisting of aliphatic diols, cycloaliphatic diols, and mixtures thereof, and optionally,
   c) additional diisocyanate selected from the group consisting of aliphatic diisocyanates, cycloaliphatic diisocyanates, and mixtures thereof, wherein said component c), when added, is added either simultaneously with component b) or separately from component b), the quantities of components a)i), a)ii), and component c) being such that the molar ratio of diisocyanate to macrodiol is from 1.5:1 to 22:1, and the reaction of components a) and b) and optionally component c) is conducted at temperatures of from 90° to 230° C., with the proviso that the reaction conditions are maintained until said polyurethane has a melt viscosity of at least 2500 mPa.s at 120° C., and optionally, said polyurethane undergoes completion of the polyaddition reaction at elevated temperatures of up to 240° C.

2. The pure polyurethanes of claim 1 which are free from catalysts.

3. The pure polyurethanes of claim 1, wherein said polyurethanes possess from 25–75% hard segment and from 75–25% soft segment.

4. A process for the production of pure polyurethanes, optionally dissolved in an organic solvent, comprising the steps of
   a) forming a pre-adduct containing NCO groups by reacting
      i) a diisocyanate selected from the group consisting of aliphatic diisocyanates, cycloaliphatic diisocyanates, and mixtures thereof, with
      ii) a macrodiol having a molecular weight of from 500 to 10,000, at temperatures of from 90°–150° C.,
   b) adding a chain extender to said pre-adduct wherein said chain extender is selected from the group consisting of aliphatic diols and cycloaliphatic diols, and, optionally,
   c) adding additional diisocyanate either simultaneously with said chain extender or separately from said chain extender, wherein said diisocyanate is selected from the group consisting of aliphatic diisocyanates, cycloaliphatic diisocyanates, and mixtures thereof, wherein the quantities of diisocyanate to macrodiol being such that the molar ratio of diisocyanate to macrodiol is from 1.5:1 to 22:1, and the addition of said chain extender, and optionally said additional diisocyanate to said pre-adduct is conducted at temperatures of from 90° to 230° C., with the proviso that the reaction conditions are maintained until said polyurethane has a melt viscosity of at least 2500 mPa.s at 120° C., 5. The process of claim 4 additionally comprising the step of
   d) heating said polyurethane to temperatures of up to 240° C. to complete the polyaddition reaction.

6. In an implant, catheter, tube, blood bag, foil for medical application, adhesive and other molded body as orthopaedic material, the improvement wherein the product is made from the pure polyurethanes of claim 1.

7. Foils, composite materials, molded bodies, sealing materials, or packaging materials comprising the pure polyurethanes of claim 1.

* * * * *